(12) United States Patent
Mendel-Hartvig et al.

(10) Patent No.: US 6,916,666 B1
(45) Date of Patent: Jul. 12, 2005

(54) METHOD USING A NEW CALIBRATOR AND A DEVICE AND TEST KIT INCLUDING THE CALIBRATOR

(75) Inventors: Ib Mendel-Hartvig, Uppsala (SE); Jörgen Gustafsson, Uppsala (SE)

(73) Assignee: Pharmacia Diagnostics AG, Uppsala (SE)

( * ) Notice: Subject to any disclaimer, the term of this patent is extended or adjusted under 35 U.S.C. 154(b) by 0 days.

(21) Appl. No.: 09/582,741

(22) PCT Filed: Dec. 30, 1998

(86) PCT No.: PCT/SE98/02464

§ 371 (c)(1), (2), (4) Date: Oct. 6, 2000

(87) PCT Pub. No.: WO99/36777

PCT Pub. Date: Jul. 22, 1999

(30) Foreign Application Priority Data

Dec. 30, 1997 (SE) .............................. 9704933

(51) Int. Cl.$^7$ ............................................. G01N 33/543
(52) U.S. Cl. ....................... 436/518; 436/169; 436/501; 435/7.1; 435/7.92; 435/7.94; 435/287.1; 435/287.7; 422/56; 422/57
(58) Field of Search ................................. 435/7.1, 7.92, 435/7.93, 7.94, 287.1, 287.7, 287.9; 436/501, 518, 523, 831, 514, 169, 808; 422/56–58

(56) References Cited

U.S. PATENT DOCUMENTS

| | | | | |
|---|---|---|---|---|
| 4,446,231 A | * | 5/1984 | Self ......................... | 435/7.91 |
| 4,657,739 A | | 4/1987 | Yasuda et al. | |
| 4,740,468 A | * | 4/1988 | Weng et al. .............. | 435/7.91 |
| 4,861,711 A | | 8/1989 | Friesen et al. | |
| 5,120,643 A | | 6/1992 | Ching et al. | |
| 5,132,097 A | * | 7/1992 | Van Deusen et al. .... | 422/82.09 |
| 5,190,654 A | | 3/1993 | Bauer | |
| 5,420,016 A | * | 5/1995 | Boguslaski et al. ........... | 435/12 |
| 5,726,064 A | | 3/1998 | Robinson et al. | |
| 6,027,944 A | * | 2/2000 | Robinson et al. .......... | 436/518 |
| 6,352,862 B1 | * | 3/2002 | Davis et al. ................ | 436/510 |

FOREIGN PATENT DOCUMENTS

| | | |
|---|---|---|
| EP | 0200381 | 11/1986 |
| EP | 253464 | 1/1988 |
| EP | 0284232 | 9/1988 |
| EP | 0420053 | 4/1991 |
| EP | 0437287 | 7/1991 |
| EP | 0462376 | 12/1991 |
| EP | 0472476 | 2/1992 |
| JP | 0253464 | 1/1988 |
| WO | WO 8808534 | 11/1988 |
| WO | WO 9406012 | 3/1994 |
| WO | WO 9516914 | 6/1995 |
| WO | WO 9622532 | 7/1996 |
| WO | WO 9709620 | * 3/1997 |
| WO | WO 9727486 | 7/1997 |

* cited by examiner

Primary Examiner—Long V. Le
Assistant Examiner—Gary W. Counts
(74) Attorney, Agent, or Firm—Dinsmore & Shohl LLP

(57) ABSTRACT

A lateral flow method for the determination of an analyte in a sample utilizes biospecific affinity reactions. The method comprises forming a complex comprising Reactant I - - - Analyte' - - - Reactant* wherein Reactant* and Reactant I exhibit biospecific affinity to the analyte, Reactant* is analytically detectable, and Analyte' is the analyte or an analyte-related reactant, determining a detectable signal from Reactant* in the complex (sample value), and obtaining the amount of analyte in a sample by comparing the sample value with one or more calibrator values, each of which corresponds to a standard amount of analyte. Before determination of the calibrator value, either calibrator or a binder for the calibrator has been bound to a matrix and is released at the determination of calibrator value. The calibrator and the analyte have the ability to biospecifically bind to Reactant* via equivalent binding sites, and one or more calibrator zones comprising calibrator or binder for the calibrator are located in the same process flow as Reactant I in a detection zone. A device for transforming measured signal values for a completed, analytically detectable reactant (Reactant*) to real amounts of analyte in a sample comprises a flow matrix in which there is an area of process flow for the transport of Reactant*, having one or more calibrator zones, an application zone for Reactant* upstream of the one or more calibrator zones, and one or more detection zones downstream of the one or more calibrator zones.

31 Claims, No Drawings

METHOD USING A NEW CALIBRATOR AND A DEVICE AND TEST KIT INCLUDING THE CALIBRATOR

TECHNICAL FIELD

The invention relates to a method associated with a process for the determination of an analyte in a sample, which process involves utilizing biospecific affinity reactions. The method includes the steps of:

i. forming a complex containing:

Reactant I - - - Analyte' - - - Reactant*, where a. Reactant* and Reactant I exhibit biospecific affinity to Analyte', and b. Reactant* is analytically detectable subsequently ii. determining the detectable signal from Reactant* in the complex (sample value), and iii. obtaining the amount of analyte in the sample by comparing the sample value with corresponding signal(s) (calibrator value(s)) from Reactant*, which has separately been allowed to bind to one or more amounts of a calibrator (calibrator amounts), each one of which corresponding to a known amount of analyte (standard amount(s)).

Analyte' is the analyte as such (in the sample) or an analyte related reactant, i.e. an added biospecific affinity reactant, included in the complex in an amount which is related to the amount of analyte in the sample. Reactant* and Reactant I can bind Analyte' at the same time. This means that they bind to spatially separated binding sites.

This type of analytical methods has been carried out in so-called flow matrices, whereby reactants including analyte are transported in a process flow through the matrix (=flow methodology) to a detection zone (DZ) where Reactant* is captured in an amount related to the amount of analyte in the sample. Capture occurs via a reactant (Capturer) which is firmly anchored to the matrix in DZ. That is, Capturer is bound via bonds which are stable under the conditions used to capture Reactant* in the detection zone. The Capturer may be Reactant I or a reactant which has biospecific affinity to Reactant I or to another reactant, which in turn, optionally via one or more additional reactants, has biospecific affinity to Reactant I.

By reactants (including analyte) exhibiting biospecific affinity (bioaffine reactants) is meant individual members of the reactant pairs: antigen/hapten-antibody; biotin-avidin/streptavidin; two complementary single chains of nucleic acid etc. As antibodies, antigen binding antibody fragments such as Fab, $F(ab)_2$', single chain Fv antibodies (scFv) etc. are considered. The reactants in question need not be naturally occurring but can also be synthetically prepared molecules/binders.

The type of test methods in question has previously been used primarily for biospecific affinity reactants where at least one part of an employed reactant pair has exhibited protein structure, in particular in connection with so-called immunochemical determination procedures.

The biospecific affinity reactions are primarily performed in aqueous media (such as water).

Previously used calibrators

Conventionally, the calibrator and analyte have often both been able to bind to Reactant*. The binding sites in question on the calibrator for binding to Reactant* often having binding properties equivalent to corresponding binding sites on the analyte. In practice this means that the calibrator and the analyte have had binding sites which are structurally equal or similar, and cross-react with each other with respect to Reactant*. Binding sites which cross-react with each other for/about a given reactant are equivalent.

Calibrator amount has in the prior art commonly been equated with standard amount.

Calibrator values, corresponding to different analyte amounts/concentrations (standard amounts), have often been compiled to a dose-response curve (calibration curve) or an algorithm.

The expression "to compare a sample value with calibrator value(s)" has also encompassed that the comparison may take place with a calibration curve and/or algorithm, corresponding to several calibrator values.

The calibrator and the analyte have often been the same substance. There are exceptions. In antibody determination one and the same calibrator has often been operational for several antibody specificities, provided that the calibrator substance has been selected such that it exhibits a constant domain of the antibody to be determined. See for example Abbott WO 97/27486.

Disadvantages of the prior art

The prior art has usually involved determination of several calibrator values in parallel with samples by running known amounts of analyte (standard amounts) in a way corresponding to samples. This has in turn led to 5–20% of all runs having been calibrator runs. By reducing the number of calibrator runs, possibly also by reducing the number of reaction steps in each calibrator run, time and consumption of reagent could be saved.

Often problems occur depending on calibrator and sample solutions having different properties and contents. This is particularly pronounced in immunological tests where the calibrator often is measured in a buffer, and the analysis of sample is performed on serum or plasma samples. A difference in contents and viscosity yields different responses (i.a. measured as "recovery" and parallelity). In addition the viscosity in a flow method becomes extra important since it influences the migration/flow velocity. This difference can be compensated for but at the same time it renders the systems more sensitive to disturbances, and thus increased inter assay variation. Other problems with tests utilizing flows are possible flow variations depending on temperature and moisture fluctuations etc.

The above problems have to some extent been overcome by the assay method disclosed in EP-A-253,464 and which uses a test zone and a reference zone on a solid phase.

OBJECT OF THE INVENTION

A first object of the invention is to improve the calibration methods presently used in tests of the kind initially mentioned.

Another object of the invention is to simplify the use of calibrators, primarily by reducing the necessary consumption of reagents needed and/or reducing the number of measurements for obtaining calibrator values.

A third object of the invention, in particular in connection with flow methods, is to enable compensation for the differences that may exist between calibrator and sample solution and between runs performed at different times and/or at different places.

THE INVENTION

We have now realized that these objects can be achieved if the calibrator is bound to the matrix before beginning the determination of calibrator value in accordance with a relevant protocol. This type of calibrator will be referred to below as a matrix calibrator. The first main aspect of the invention is therefore a method in accordance with the procedure mentioned initially, and which has the characterizing feature that the calibrator, or a reactant capable of binding to the calibrator, has been bound to a matrix which is insoluble in the liquid medium in which binding of Reactant* to the calibrator occurs, before beginning the determination of a calibrator value. This means that the calibrator or the calibrator binder, respectively, usually has been bound to the matrix already by the manufacturer, such that the matrix calibrator is delivered as a ready component in a kit. The binding between calibrator and matrix normally is of another kind than that obtained between Analyte' and Reactant I when running a sample.

Matrix calibrators provide great advantages, if transport of Reactant* to the calibrator occurs by means of a flow (process flow) in a so-called flow matrix to a zone in the matrix, which contains the matrix calibrator or the calibrator binder (calibrator zone, CZ).

When a calibrator binder is bound to the matrix, the calibrator may be either movably (diffusively) pre-deposited in the matrix in a zone separated from the detection zone, or it may be added together with or separately from the sample.

The calibrator binder is usually one member of a specific binding pair (reactant pair), the other member of the binding pair being coupled or conjugated to the calibrator substance. Such specific binding pairs are well-known to a person skilled in the art, and as examples may be mentioned: immunological binding pairs, such as antigen-antibody and hapten antibody, biotin-avidin or -streptavidin, lectin-sugar, hormone-hormone receptor, nucleic acid duplex.

Flow matrices

The flow matrix defines the space in which the reactants are transported. Thus, the matrix may be the inner surface of a single flow channel (such as a capillary), the inner surface of a porous matrix having a system of flow channels (porous matrix) etc. extending through. This type of matrices is called flow matrices. The matrices may exist in the form of monoliths, sheets, columns, membranes, single flow channels having capillary dimensions, or aggregated systems of such flow channels etc. They may also exist in the form of particles packed in column casings, compressed fibers etc. The inner surface of the matrix, i.e. the surface of the flow channels, should be hydrophilic, such that aqueous media (primarily water) may be absorbed and transported through the matrix. The minimum inner dimension of the flow channels (measured as a diameter for channels having a circular cross section) should be sufficiently large for allowing transport through the matrix of the reactants being used. The rule of thumb is that suitable matrices are selectable among those having flow channels with the smallest inner dimension in the interval 0.4–1000 $\mu$m, preferably 0.4–100 $\mu$m if the matrix has a system of mutually communicating flow channels. Flow channels having a smallest inner dimension in the upper part of the broad interval (up to 1000 $\mu$m) are primarily of interest for flows driven by an externally imposed pressure/suction.

Matrices of interest are often built up from a polymer, e.g. nitrocellulose, nylon etc. The material in the matrix as well as the physical and geometrical design of the flow channels may vary along the flow, depending on what a certain part of the matrix is to be used for (Pharmacia AB WO 96/22532; Medix WO 94/15215).

Along the flow in the matrix there may be one or more defined zones for application of sample, reactants, buffer etc. ($A_SZ$, $A_RZ$, $A_BZ$ etc.), and one or more zones for calibrator and/or detection (CZ and DZ, respectively).

Various flow matrices that may be used in the type of tests in question are described in previous patent publications. See e.g. Behringwerke U.S. Pat. No. 4,861,711, Unilever 88/08534, Abbott U.S. Pat. Nos. 5,120,643 and U.S. Pat. No. 4,740,468, Becton Dickinson EP 284,232 and U.S. Pat. No. 4,855,240; Pharmacia AB WO 96/22532.

Process flow

The direction of the flow is from a zone of application of sample and/or reactant and towards existing calibrator and detection zones (CZ and DZ, respectively). Precisely which zones the process flow is to pass is determined by the test protocol in question. A process flow may start from a point with a radial spread and a flow front in the form of a circular periphery or a part thereof. A process flow may also start from a zone in the form of a band and may have a straight flow front perpendicular to the direction of flow.

In a less preferred variant, the process flow proceeds from an application zone for Reactant*, which at the same time is a calibrator zone or a detection zone. In this variant the flow is preferably radially spread from the zone of application, and may pass additional calibrator zones and/or detection zones.

Flow through the matrices may be achieved by influence from capillary forces, e.g. by starting off with a substantially dry matrix. A sucking body may be placed at the very end of the flow as an aid. By means of an imposed electrical field, dissolved components may be transported from the zone of application to a detection/calibrator zone.

The utilized flow is preferably lateral, i.e. parallel with the upper surface of the matrix. Also other types of flows, such as in depth in the matrix, may be used.

Calibrator and detection zones in flow matrices

The flow matrix used in the preferred embodiment exhibits one or more distinct zones with calibrator (calibrator zones, CZ1, CZ2, CZ3 etc.). Each calibrator zone contains matrix calibrator in an amount such that the measurement signal from Reactant* (calibrator value), detected in the zone when a flow passes, distinctly corresponds to a certain amount of analyte in the sample (standard amount).

The calibrator may be selected in the same way as previously was the case for the types of tests in question. Using flow methodology and arranging for sample (the analyte) to be transported through a calibrator zone, the calibrator should be selected such that it does not bind to the analyte. If the calibrator is able to bind analyte it imposes special requirements on the position of the calibrator zone in relation to the zone of application of sample. See below.

The amount of calibrator that has bound to a calibrator zone does not need to be the same as the corresponding standard amount. This is because the binding activity in relation to Reactant* often is changed, when the sample substance is bound to a matrix.

If it is desirable to determine antibodies with different specificity but from the same species, of the same Ig class or Ig subclass, it is preferred that the calibrator exhibits a binding site which is unique for the species, the class, or subclass. As a rule this means that a calibrator for determination of antibodies exhibits an epitope which is present in a constant domain of the antibodies in question, for mammal antibodies primarily a part of Ig(Fc).

One and the same matrix may exhibit one or more detection zones (DZ1, DZ2, DZ3 etc.) together with one or more calibrator zones. In the detection zone, complexes containing Analyte' and Reactant* bind to the matrix via the initially mentioned Capturer, which is firmly fixed in a DZ. If Reactant I binds to the matrix via the Capturer, Reactant I need not be immobilized in the matrix from the start but may either be movably (diffusively) pre-deposited in the matrix in an area or zone separated from the detection zone, or it may be added together with or separately from the sample.

If there are several calibrator and/or detection zones in the same flow matrix, the greatest advantages with the invention are achieved if several of the zones are located along the same process flow.

If there are several detection zones (DZ1, DZ2, DZ3 etc.) in one and the same matrix, these may correspond to different analytes. One can utilize the same calibrator for analytes having equivalent binding sites. If the analytes lack equivalent binding sites one calibrator is required for each analyte. If all analytes have the same equivalent binding site the simpliest condition will be at hand. The same calibrator, the same calibrator zones and the same Reactant* may then be utilized for all analytes.

Calibrator zones and detection zones may be geometrically designed in various manners (rectangular, circular, linear, dot-shaped etc.). The zones may have different configurations relative to each other. Good configurations are such wherein a common flow consecutively or simultaneously penetrates several zones, in particular zones of different kinds (DZ and CZ). An example of consecutive penetration is parallel zones located after each other in the same process flow. An example of simultaneous penetration is zones located next to each other on the same circular periphery, where the process flow is radially spread from the centre of the corresponding circle. Combinations of these variants may be used, i.e. apart from zones on a circular periphery there are also zones on the periphery of circles which are concentric with the first-mentioned circular periphery. Simultaneous penetration may also be achieved with a straight flow front having detection and calibrator zones located next to each other at the same distance from the starting point of the process flow.

If several detection zones and/or calibrator zones are located in the same process flow, a measurement signal for these zones may be obtained in one and the same test run/reagent application. If there are several calibrator zones in the same process flow, a dose-response curve (calibration curve) or algorithm may be set up for the values obtained for the same application of Reactant*. A calibrator zone that exists together with a detection zone in the same flow may function as a positive internal calibrator (PIC).

In one variant a matrix is utilized exhibiting at least one calibrator zone (CZ1, CZ2, etc. (positive internal calibrators)) and at least one detection zone (DZ1, DZ2, etc.) in combination with one or more separately obtained calibrator values. The separately obtained calibrator values need not refer to the same conditions under which the sample is to be run. To the extent separate matrix values, calibration curve and algorithm are intended to be used during a longer period of time, reference is made to master values, master curve and master algorithm, respectively.

The use of separately obtained calibrator values involves:
i. letting sample and Reactant* pass a detection zone (DZ) and a positive internal calibrator (PIC, CZ) in a matrix exhibiting both DZ and CZ,
ii. determining the measurement signal from a CZ (PIC value, CZ) and from DZ,
iii. comparing the PIC value with corresponding separately obtained calibrator value(s), whereby any deviations are a measure of deviations between the conditions under which the sample has been run, and the standard conditions applying to the separate calibrator value(s),
iv. adapting the measured signal for the sample (sample value) to the conditions applicable for the separately obtained calibrator values, and then
v. obtaining the amount of analyte in the sample by comparing the adapted measurement signal for the sample with the separate calibrator value(s).

Alternatively, one may adapt the separate calibrator values to deviations in conditions and then directly compare a measured sample value with adapted calibrator values. This is equivalent to the steps (iv) and (v) above (called vice versa in claims). In the steps (iv) and (v) it is, of course, included as an alternative to adapt the corresponding calibration curve or algorithm in order to calculate the level of analyte by comparing the sample value with either of these.

What has been said above, applies, of course, also to the case that a binder for the calibrator has been bound to the calibration zone(s) of the matrix.

A calibrator and detection zone in the same process flow will reduce previous sources of error having been caused by differences in sample and calibrator. A positive internal calibrator and several calibrator zones in the same process flow will completely or partly compensate for variations in flows between separate runs. The spread in the measurement result should be lower while internal as well as external factors may be compensated for completely or partly. The problem with sample and calibrator having different compositions is eliminated. For near patient tests, the internal calibrator will be able to provide a well defined limit as to what constitutes a positive response, and to provide the quality assurance which today is missing for these types of tests.

The anchoring of the calibrator to the matrix may take place via covalent bonding or via physical adsorption, biospecific affinity etc. Like prior art in this field the invention may utilize combinations of binding types, such as covalent bonding to the matrix of a biospecific affinity reactant directed to the calibrator. Specifically, physically adsorbed or covalently bonded streptavidin in combination with a biotinylated calibrator may be mentioned, or a similarly bound antibody directed to the calibrator. Anchoring of the calibrator to the matrix may take place via particles having been deposited in/on the matrix, and to which the calibrator is covalently, physically adsorptively or biospecifically etc. bound. The particles attach to the matrix either because their size has been selected such that they cannot be transported through the matrix, or via physical adsorption. See i.a. Abbott/Syntex U.S. Pat. No. 4,740,468; Abbott EP 472,376; Hybritech EP 437,287 and EP 200,381; Grace & Co EP 420,053; Fuji Photo Film U.S. Pat. No. 4,657,739; Boehringer Mannheim WO 94/06012.

The Capturer may be bound to a detection zone according to the same principles as those applying to a calibrator. In one and the same process flow a calibrator and Capturer may be bound to their respective zones in the same way or in different ways. What has been said above concerning the anchoring of the calibrator and the Capturer, is, of course, also applicable to the anchoring of a binder for the calibrator substance. For example, the above mentioned combination of a biotinylated calibrator substance and physically or covalently bound streptavidin may be used.

Zone of application of sample ($A_sZ$)

The zone of application of sample may be located upstream or downstream in relation to calibrator zones, preferably upstream. In case the matrix calibrator has been selected such that it binds analyte, the zone of application of sample must be located downstream of the matrix calibrator. In relation to detection zones the zone of application of sample should always be located upstream in useful embodiments.

In certain less preferred embodiments it is conceivable to apply sample in a calibrator or detection zone.

Zone of application of Reactant* ($A_{R*}Z$) and other biospecific affinity reactants ($A_RZ$)

An application zone for Reactant* ($A_{R*}Z$) should always be located upstream of the calibrator zones.

If there is a detection zone in the process flow, the order of the zones of application of biospecific affinity reactants should ensure that Analyte' is transported into its detection zone before or simultaneously with Reactant*. One or more reactants may be added in the same zone of application. If the zone of application is common to sample and at least one reactant, let us say Reactant*, application may occur simultaneously, e.g. by having mixed a sample and a reactant before they are applied in the zone. If desired, the mixture may be preincubated such that the reactant will bind to the analyte or to other components in the sample, as intended, before application of the sample. Having knowledge of various protocols, the skilled person will be able to easily determine which zones he needs and the possible order thereof.

If Reactant I is present in dissolved form, the matrix has a zone of application for it at the same time as there is a Capturer firmly fixed in the detection zone. If the Capturer requires additional biospecific affinity reactants in order to bind Reactant I (see under "Technical field"), there are zones of application for these reactants. Zones of application for Reactant I, when it is not a Capturer, and any additional reactants must be positioned such that Reactant I reaches the detection zone before or at the same time as Analyte'. If Reactant I is in soluble form, the Capturer may preferably be one member of a specific binding pair, the other member of which is coupled or conjugated to Reactant I. Exemplary specific binding pairs are immunological binding pairs, such as antigen-antibody and hapten-antibody, biotin-avidin or -streptavidin, lectin-sugar, hormone-hormone receptor, nucleic acid duplex.

If both the calibrator and Reactant I are in soluble form to then bind to the matrix via specific binding pairs, these two binding pairs are, of course, different.

In certain less preferred embodiments biospecific affinity reactants (inclusive Reactant*) may be applied in a calibrator or detection zone. See under the heading "Process flow".

Reactants utilized in the method may be predeposited in their respective zone or may be added in connection with performing the method of determination. Predepositing involves application of the reactant in question in advance in such a way that it will not spread outside its zone of application until a flow of liquid is initiated in or passes the zone.

Predeposition of reactants may take place by methods known per se. See for example (Behringwerke U.S. Pat. No. 4,861,711; Unilever WO 88/08534; Abbott U.S. Pat. No. 5,120,643; Becton Dickinson EP 284,232). It is important to take into consideration the fact that a predeposited reactant should easily dissolve when liquid passes through the zone of application in question. In order to achieve quick dissolution it is common to incorporate/codeposit reactants in/with substances that quickly dissolve. This type of substances are often hydrophilic having polar and/or charged groups, such as hydroxy, carboxy, amino, sulphonate etc. In particular there may be mentioned hydrophilic quickly soluble polymers, e.g. having carbohydrate structure, simple sugars including mono-, di- and oligosaccharides and corresponding sugar alcohols (mannitol, sorbitol etc.). It is common practice to first coat the zone of application in question with a layer of the quickly soluble substance, whereupon the reactant is applied, possibly followed by one additional layer of quickly soluble substance. An alternative way is by incorporating the reactant in particles of quickly soluble material, which then is deposited in the zone in question of the matrix.

Zones for buffer ($A_BZ$)

Buffer systems that are required may be included in solutions added simultaneously with samples and reactants. In conventional techniques addition of buffer takes place in the zone of application that is located upstream of all other zones of application. This has often been equal to the sample application zone. In the present invention buffer may in principle be added in an optional position along the flow of transport. See below.

In a co-pending PCT application "Analytical method comprising addition in two or more positions and a device and test kit therefor" (based on SE 9704934-0) there is disclosed an invention, which in one variant provides a preferred embodiment of the present invention. This application is hereby incorporated by reference in the present text. The invention in this separate patent application is based on the discovery that liquid from two subsequent zones (AZ2 and AZ1) in a flow matrix may migrate after each other without mixing. This will be achieved if liquid is applied to the zone (AZ1) located downstream before or essentially simultaneously with application of liquid to the zone (AZ2) located upstream. This discovery has led to the ability to achieve zonewise migration of any reactants present in the liquids, towards a detection zone. If the zone of application of sample ($A_SZ$) is located downstream of the zone of application of Reactant* ($A_{R*}Z$), and if liquid is applied to $A_{R*}Z$ and sample to $A_SZ$, the analyte may migrate into the detection zone before the liquid containing Reactant* does. If there is one zone of application for liquid alone (buffer) ($A_BZ$) between $A_{R*}Z$ and $A_SZ$, a wash of the detection zone DZ is obtained between capture of analyte and Reactant*. Such an intermediate buffer zone ($A_BZ$) may also ensure that a reactant (including analyte), that is applied in a zone located downstream, reaches DZ before a reactant, starting from a zone of application located upstream. The latter may be important if the matrix as such retards the reactant that has been applied in the zone located downstream.

Reactants may be included in the liquid that is applied to a zone. Alternatively they may be pre-deposited in the zone where the corresponding liquid is to be applied, or in a zone that is located between this and the nearest zone that is located downstream, for application of liquid. Sample (the analyte) normally is applied in the form of liquid.

This embodiment of the invention is particularly interesting for sequential methods of the type is question in flow matrices, i.e. methods wherein the matrix in addition to a calibrator zone also contains a detection zone, and where the sample/analyte is to be transported into the detection zone before liquid containing Reactant*.

Analytically detectable reactant (Reactant*)

Usually analytical detectability of a reactant is obtained because it comprises an analytically detectable group. Well-known examples of often used groups are enzymatically active groups (enzyme, cofactor, coenzyme, enzyme substrate etc.), fluorophore, chromophore, chemiluminescent, radioactive groups etc. Groups being detected by means of a biospecific affinity reactant are also usually referred to this category, e.g. biotin, hapten, Ig-class, Ig-subclass and Ig-species specific determinants etc. In this invention, particles the surfaces of which have been coated with a biospecific affinity reactant have proved to be particularly good.

The particles may contain any of the previously mentioned detectable groups, such as fluorophore groups, or they may be coloured (=containing chromogenic groups). Useful particles often have a size in the interval 0.001–5 μm, preferably 0.01–5 μm. The particles may be spherical and/or monodisperse or polydisperse. They may have colloidal dimensions, so-called sol (i.e. usually spherical and monodisperse having a size in the interval 0.001–1 μm). Well-known particulate label groups are metal particles (such as gold sol), non-metal particles (such as $SiO_2$, carbon, latex and killed erythrocytes and bacteria). In certain cases it has been emphasized that the particles should be non-sedimentable under the utilized conditions. (See Pharmacia AB, WO 96/22532).

See also Unilever, WO 88/08534; Abbott, U.S. Pat. No. 5,120,643; Becton Dickinson, EP 284,232.

In connection with the development of matrix calibrators we have surprisingly found that good results may be obtained if one simultaneously utilizes:

(a) Reactant* where the detectable group is particles as disclosed above, and (b) a detection zone in which the Capturer attaches to the matrix via particles (anchoring particles), having dimensions that would allow transport of the particles through the matrix.

We have achieved a functioning system wherein label particles and anchoring particles have had substantially the same dimensions, which means that in all probability the label particles may be larger than the anchoring particles and vice versa, as long as they remain smaller than the flow channels defined by the matrix. The system may function with as well as without predeposition of Reactant*. This embodiment is described in more detail in a co-pending PCT-application "Analytical method using particles and test kit for performing the method" (based on SE 9704935-7). Also this latter application is incorporated by reference. Applied to the present invention this means that Reactant* has particles as an analytically detectable group according to a above, and that the calibrator and/or the Capturer binds to the matrix via particles according to b above.

Relevant test protocols

The invention may primarily be applied to non-competitive (non-inhibition) test variants, but also to competitive (inhibition) test variants, if these involve that a complex is formed with an analyte-related reactant bound between Reactant I and Reactant*. The protocols may be run as simultaneous or sequential variants. By simultaneous methods is meant that Reactant* and Analyte' are co-transported during at least a part of the transport towards the detection zone, and preferably reach the latter simultaneously. By sequential method is means that Analyte' during at least a part of the transport towards the detection zone migrates in front of Reactant*, and preferably reaches the detection zone before Reactant*. Illustrative examples are given below. "-" relates to firm anchoring to the matrix from the start. " - - - " relates to binding via biospecific affinity. It has been assumed that the reactants are monofunctional with regard to the binding sites being utilized.

A. Sandwich protocol: Reactant I (=Capturer) and Reactant* have biospecific affinity to the analyte (=Analyte'). x is the number of moles of Reactant I on the matrix. y is the number of moles of Analyte' (=moles of Reactant*) that has been captured on the matrix via Reactant I.

Formed complex:

B. Sandwich protocol: Reactant II (=Capturer) has biospecific affinity to Reactant I, which in turn has biospecific affinity to the analyte (=Analyte'). Reactant* has biospecific affinity to the analyte. x is the number of moles of Reactant II on the matrix. y is the number of moles of Analyte' (=moles of Reactant*) that has been captured on the matrix via Reactant II - - - Reactant I. z+y is the number of moles of Reactant I that has been captured on the matrix via Reactant II.

Formed complex:

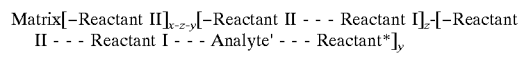

C. Protocol of inhibition type: Reactant I is an analyte analogue (=Capturer) and has binding sites that are equivalent with the binding sites on the analyte. Analyte' is a reactant that has biospecific affinity to the analyte and to Reactant I. Reactant* has biospecific affinity to Analyte'. Analyte' is included in the formed complex in an amount that is related to the amount of analyte in the sample. x is the number of moles of Reactant I on the matrix. y is the number of moles of Analyte' (=number of moles of Reactant*) that has been captured on the matrix via Reactant I.

Formed complex:

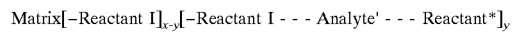

Analytes in sample

The invention is primarily adapted for determination of bio-specific affinity reactants (analytes) of the types mentioned initially. Great advantages are obtained for analytes occurring in multiple forms, which have as a common denominator at least one binding site with equivalent binding properties.

For non-competitive methods (sandwich) the analyte may be an antibody directed to an antigen (including allergen), or hapten (Test protocols A and B above). Reactant I in this case is the antigen or the hapten to which the antibody is directed, and Reactant* is an antibody directed to the analyte. Alternatively Reactant* is the antigen or the hapten, and Reactant I is an antibody directed to the analyte. For non-competitive methods the analyte may also be an antigen, Reactant* and Reactant I being antibodies directed to the antigen. As examples of analyte-antigen may be mentioned immunoglobulin, possibly of a particular Ig class or Ig subclass. When the analyte is an antibody or an immunoglobulin, Reactant* and Reactant I, respectively, may exhibit biospecific affinity towards an Ig determinant that is specific for an Ig class such as IgA, IgD, IgE, IgG or IgM and/or for a subclass if present (e.g. IgG1, IgG2, IgG3 or IgG4), and/or for a certain species. This means that Reactant* and Reactant I, respectively, normally is an antibody exhibiting some of these specificities when the analyte is an antibody or an immunoglobulin.

Competitive variants are primarily applicable to low molecular analytes. In the test protocol C above the analyte may be an antigen/hapten, in which case Reactant I is the antigen/hapten bound to the matrix, Analyte' is an antibody directed to the antigen/hapten, and Reactant* is an antibody directed to Analyte'.

It has been particularly interesting for the inventors to be able to measure analytes the occurrence and/or amount of which being related to autoimmune diseases and allergy. It is particularly interesting to measure anti-allergen antibodies of IgE of IgG class, for the latter preferably with emphasis on some of the mentioned subclasses. Measurement of allergen specific antibodies may be employed in connection with diagnosing of IgE mediated allergy.

Samples

Relevant samples may be of biological origin, e.g. from different body fluids (whole blood, serum, plasma, saliva, urine, tear liquid, cerebrospinal fluid etc.), extracts from biological tissue, from cell culture media, processing procedures in biotechnology, from foodstuff, from the environment (environmental analysis samples) etc. The samples may be pretreated in order to fit e.g. the matrix, the test protocol involved etc.

A second aspect of the invention

This aspect of the invention relates to a test device where the matrix calibrator constitutes a central point. The matrix calibrator is used in analytical methods for transferring measured signal values (sample values) for a complexed, analytically detectable reactant (=Reactant*) to real amounts of analyte in a sample, in connection with performing an analytical method utilizing biospecific affinity reactions. As in the method aspect Reactant* is complexed in an amount that is related to the amount of analyte in a sample. The most important type of analytical methods for which the device may be used are those for which the method of the invention is used, that is methods where one forms complexes comprising Reactant I - - - Analyte' - - - Reactant*. Reactant I, Analyte', Reactant* and - - - have the same meanings as in the method aspect.

The device is characterized by exhibiting:

a) a flow matrix in which there is an area of process flow for transport of Reactant*, and in that this area comprises i. one or more calibrator zones (CZ1, CZ2 etc.) comprising a calibrator, or a binder for the calibrator, that is firmly anchored to the matrix, the amounts of calibrator or calibrator binder, respectively, being different for at least two calibrator zones, and the calibrator exhibiting binding sites to which Reactant* may bind, when Reactant* is transported through a calibrator zone, and ii. an application zone for Reactant* ($A_{R*}Z$) located upstream of said one or more calibrator zones.

If the calibrator zone/zones instead of the calibrator contains a binder for calibrator substance, the device preferably also contains:

b) calibrator which is movably (diffusively) predeposited in or downstream of $A_SZ$.

Preferably, the device is included in a kit which comprises:

c) Reactant* which may be predeposited in $A_{R*}Z$.

The process flow may also contain (a) a detection zone (DZ) located downstream or coinciding with $A_{R*}Z$, and in which there is a firmly fixed Capturer via which Reactant* may bind to DZ, and (b) a zone of application for sample ($A_SZ$) located upstream or coinciding with said DZ. $A_{R*}Z$ may be located upstream or downstream or coincide with $A_SZ$ (if present), preferably upstream or downstream. If $A_SZ$ and DZ are present in the same process flow as the calibrator zone, $A_SZ$ is preferably located upstream and DZ preferably downstream of existing calibrator zones.

In preferred embodiments the firmly anchored reactant (Capturer) has biospecific affinity to the analyte or to an analyte-related reactant that may be analytically detectable. Analyte related reactant is primarily relevant to competitive test variants.

Calibrator substance is selected in the same way as in the method aspect of the invention. In those cases where the selected calibrator substance exhibits biospecific affinity to the analyte, the corresponding calibrator zone shall be located upstream of $A_SZ$.

Additional details regarding calibrators, zones, reactants, matrices, process flows, test protocols, samples etc. are apparent from the description of the method aspect of the invention.

The invention will now be illustrated with a number of examples showing various preferred embodiments thereof. The invention is defined by the attached claims and what is disclosed in the description.

EXAMPLE 1

Determination of Birch Specific IgE with Carbon Particle Conjugate and with Calibrator Bound to the Matrix Methods and materials Adsorption of phenyldextran to polystyrene particles: Phenyldextran (degree of substitution: 1 phenyl group on each fifth monosaccharide unit=20%, Mw dextran 40,000, Pharmacia Biotech AB, Uppsala, Sweden) was adsorbed to polystyrene particles (0.49 μm Bangs Laboratories, USA) by incubations under stirring with phenyldextran dissolved in deionized water to 1) 5 mg/ml, 10% particle suspension, RT 1 h, 2) 5 mg/ml, 5% particle suspension, RT 1 h, 3) 20 mg/ml, 1% particle suspension, RT overnight 15 h. The particles were subsequently washed twice with deionized water. The particle suspensions were centrifuged between each incubation and wash (12,100×g, 25 min, Beckman, J-21, JA-20, 10,000 rpm). The particle suspension was finally sonicated (Ultrasonic bath, Branson 5210, 5 min).

Coupling of human IgE (hIgE) to polystyrene particle (=hIgE particles): Human IgE was coupled to phenyldextran coated polystyrene particles with CDAP (1-cyano-4-dimethylamino-pyridinium bromide (Kohn J and Wilchek M, FEBS Letters 154(1), (1983) 209–210).

Desalting and change of buffer of hIgE were performed by gel filtration (PD-10, Pharmacia Biotech AB, Sweden) in $NaHCO_3$, 0.1 M, pH 8.5. 278 mg of polystyrene particles (as above) in 2% solution in 30% (by volume) acetone were activated with 4.2 ml CDAP (0.44 M) and 3.4 ml TEA (0.2 M triethylamine, Riedel-de Haen, Germany). CDAP was added during stirring for 60 s and TEA during 120 s. The particles were washed with 30% (by volume) acetone and centrifuged at 12,100×g (25 min, Beckman, J-21, JA-20, 10,000 rpm). 25 mg of hIgE were coupled to the activated particles in incubation with stirring overnight at +4° C. Then the particles were centrifuged before deactivating with glutamic acid 0.05 M and aspartic acid 0.05 M in $NaHCO_3$ buffer. Incubation was performed with stirring overnight at +4° C. Coupled particles were washed with 0.1 M $NaHCO_3$ and twice with 20 mM borate buffer pH 8.5. The particle concentration was determined spectrophotometrically at $A_{600}$ nm with untreated particles as reference. Concentration of coupled protein was determined by having radioactive human IgE present during coupling.

Extraction of t3 (birch pollen, *Betula verrucosa*): 1 part (weight) of birch pollen (Allergon, Sweden) was extracted with 10 parts (volume) 0.1 M of phosphate buffer (denoted 1/10), pH 7.4. The extraction lasted for 2 hours on a shaker table at +4° C. The extract was centrifuged at 4000 rpm for 1.75 h. After filtering the solution was applied to a PD-10 column and eluted in 0.1 M $NaHCO_3$, pH 8.5 (denoted 1/14).

Coupling of t3 extract to a polystyrene particle (t3 particles: t3 extract (1/14) was coupled with CDAP (Kohn and Wilchek, FEBS Letters 154(1) (1983) 209–210) to polystyrene particles coated with phenyldextran. Polystyrene particles (400 mg, coated with phenyldextran as above) in 30% (by volume) acetone, 2% particle suspension, were activated with 60 mg of CDAP (100 mg/ml in 30% acetone) and 0.48 ml 0.2 M triethylamine (Riedel-de Haen, Germany). CDAP was added with stirring and TEA was added dropwise during 90 seconds and stirring for 120 s in total. The reaction was quenched by the addition of 30% acetone (4 times volume) and centrifuging at 12,400×g for 35 min. The particles were washed once with deionized water. 32 ml of t3 extract in 0.1 M NaHCO$_3$, pH 8.5, were added to 80 mg of the activated particles and coupling was continued for 1 hour on a shaker table. Then the particles were centrifuged before they were deactivated with 0.05 M aspartic acid och 0.05 M glutamic acid in 0.1 M NaHCO$_3$, pH 8.5. Incubation on shaker table overnight at +4° C. The particles were washed by centrifuging in 1) 0.1 M NaHCO$_3$, 0.3 M NaCl, pH 8.5; 2) 0.1 M Na acetate, 0.3 M NaCl, pH 5; 3) 0.1 M NaHCO$_3$, pH 8.5; and 4) 20 mM Na borate, pH 8.5.

The particle concentration was determined spectrophotometrically at 600 nm with uncoated polystyrene particles as reference.

Adsorption of anti-human IgE antibody to carbon particles (carbon particle conjugate=Reactant*): Monoclonal anti-hIgE was adsorbed to carbon particles (sp100 from Degussa, Germany). See Pharmacia AB, WO 96/22532. The ready suspension was diluted with buffer to 400 μg of carbon particles per ml.

Deposition of t3 particles on membrane in a detection zone: One sheets on nitrocellulose with polyester backing (Whatman, 8 μm, 5 cm wide) 4% of the above-mentioned t3-coupled particles were applied with Linear Striper (IVEK Corporation) with a flow of 1 μl/s and 1 μl/cm as a straight zone. The sheets were dried for 1 hour, 30° C., whereupon the sheets were cut at right angles relative to the zone to 0.5 cm wide strips (Matrix 1201 Membrane Cutter, Kinematics Automation).

Deposition of hIgE particles in calibrator zones: On nitrocellulose sheets with polyester backing (Whatman, 8 μm, 5 cm wide) hIgE particles were deposited as parallel calibrator zones with Linear Striper (IVEK Corporation, USA). The flow was 1 μl/s and 1 μl/cm. Sheets intended for strips having only calibrator zones were coated with six parallel zones. hIgE concentrations in the zones were 0, 0.84; 3.4; 14; 54.2 and 217 ng hIgE/0.5 cm. Before performing the deposition the hIgE particles were diluted in borate buffer (20 mM, pH 8.5, Dextran T5000 4.2% w/w, sorbitol 5.8% w/w). All zones also comprised 1% phenyldextran-coated particles in order to yield the same amount of particles in each zone. On a separate nitrocellulose sheet there was deposited a zone with hIgE particles (14 ng hIgE/0.5 cm, PIC=positive internal calibrator), and in a parallel zone t3 particles as above (detection zone). The deposition took place with the same parameter as for hIgE particles. The sheets were dried 1 h, 30° C., and were then cut, perpendicularly relative to the zones, to strips 0.5 cm wide (Singulator: Matrix 1201 membrane cutter, Kinematic automation, USA).

Test procedure: Strips were mounted on a plane plastic surface. At the top (0.5 cm) on the strip a sucking membrane was placed (width 3 cm, Whatman, 17 Chr). To obtain a constant pressure metal weights were put on the sucking membranes. 10 mm from the lower edge a 2 mm wide Inplastor strip was mounted (preglued polyester film). The Inplastor strip should prevent applied liquids from flowing out over too large a portion of the membrane. To the lower end of the strip there was applied 30 μl of sample or buffer in the alternative. After suction of the sample volume the following components were applied in the given order: 15 μl buffer, 15 μl carbon particle conjugate as above and 30+30 μl buffer. The buffer was: NaPO$_4$ 0.1 M, BSA 3%, NaN$_3$ 0.05%, sucrose 3%, NaCl 0.5%, phenyldextran 0.25%, bovine gammaglobulin 0.05%, pH 7.5. The degree of blackening of the reaction zones was measured as absorbance with ultroscan (Ultroscan XL, Enhanced Laser Densitometer, LKB).

Results

A) Activity determination on deposited IgE calibrator curve against IgE calibrators (24° C.) run as samples on separate strips with anti-hIgE antibody in the binding zone.

TABLE 1

| | Deposited amount IgE | Calculated KU/L | Abs (x1000)* |
|---|---|---|---|
| 1 | 0.84 | 0.27 | 46 |
| 2 | 3.4 | 0.48 | 109 |
| 3 | 14 | 0.71 | 266 used below as positive internal calibrator |
| 4 | 54.2 | 2.7 | 619 |
| 5 | 217 | 66.3 | 1882 |

*= absorbance on a reaction zone after carbon particle conjugate having bound.

B) Determination of birch specific IgE antibody in patient samples run at 18, 24 and 37° C., with and without positive internal calibrator (PIC) in order to adjust the standard curve (run at 24° C.).

TABLE 2

Results (KU/L) with and without corrected calibrator curve:

| | Corrected | | | Not corrected | | |
|---|---|---|---|---|---|---|
| | 18° C. | 24° C. | 37° C. | 18° C. | 24° C. | 37° C. |
| Sample 1 | 1.3 | 1.1 | 1.4 | 0.83 | 1.1 | 1.8 |
| Sample 2 | 6.9 | 5.5 | 6.7 | 5.1 | 8.6 | 20 |

The results show that it is possible to compensate for the variation in the separate runs by using positive internal calibrators. In addition the results show that it is possible to use predeposited calibrators.

The embodiment shown in this example may be modified such that one or more of the following criteria are met, (a) has predeposited Reactant* in a zone of application and/or (b) has a zone of application of sample located downstream or upstream of the zone of application of Reactant*, (c) has zones allowing simultaneous addition of Reactant* and sample.

EXAMPLE 2

Determination of Birch-Specific IgE with Fluorescent Detection Particles and with a Calibrator Predeposited in the Application Zone Methods and materials Coupling of streptavidin to polystyrene particles: Streptavidin (Amersham Pharmacia Biotech AB, Sweden) were covalently coupled to phenyldextran-adsorbed polystyrene particles with CDAP (1-cyano-4-dimethylaminopyridinium bromide) (Kohn J and Wilchek M, FEBS Letters 154 (1) (1983) 209–210), according to the description in Example 1 above for hIgE. The coupled particles were washed three times with 50 mM NaPO$_4$, 0.05% NaN$_3$, pH 7.4. The particle concentration was determined spectrophotometrically at A600 nm with untreated particles as reference.

Deposition of streptavidin-coupled particles on nitrocellulose membranes: To nitrocellulose sheets with polyester backing (Whatman, 8 μm, 5 cm wide) were applied with Linear Striper (IVEK Corporation) zones of:

1) streptavidin-coupled particles diluted to 1% particle content i 10 mM NaPO$_4$, 5% sucrose, 5% dextran T5000, 0.01% NaN$_3$, pH 7.4;

2) t3-coupled particles, prepared according to Example 1, diluted to 4% particle content in 50 mM NaPO$_4$, 10% sucrose, 0.05% NaN$_3$, pH 7.4. The deposition flow was 2.5 µL/cm and the rate was 20 mm/sec.

The deposits were dried for 1 hour at 30° C., and the sheets were cut to 0.5 cm wide strips (Matrix 1201 Membrane Cutter, Kinematics Automation).

Coupling of anti-hIgE antibodies to detection particles: Antibodies to hIgE which had been cleaved with pepsin to fab'2 fragments were coupled to fluorescent polystyrene particles having aldehyde groups on their surface (Molecular Probes C-17177 TransFluoSpheres, aldehyde-sulphate microspheres, 0.1 µm, 633/720, 2% solids). 23 mg of antibody were then coupled to 66 mg of particles in 50 mM NaPO$_4$ buffer, pH 6.5, overnight at room temperature, whereupon 205 µL of NaCNBH$_4$ (5 M) were added to reduce the coupling for 3 hours at room temperature. Centrifugation was performed at 20,800×g (50 min in Eppendorf 5417R, 14,000 rpm), and deactivation in glutamic acid 0.05 M and aspartic acid 0.05 M in deionized water, pH 6.5, was then carried out overnight with stirring at room temperature. After centrifugation at 20,800×g for 50 min, blocking was performed with 0.2% BSA in 50 mM NaPO$_4$, pH 7.4, with 0.05% NaN$_3$, and incubation took place at +4° C. Centrifugation was then performed again at 20,800×g for 50 min followed by two washes with blocking buffer which was then also used for storage. The particle concentration was determined in a fluorimeter (Perkin-Elmer LS50B) with a standard curve prepared with the original particle. The coupled protein during the coupling was determined by having radioactive anti-hIgE present during the coupling.

Biotinylation of hIgE: Biotinylation of hIgE was performed according to the conditions recommended by the supplier (Pierce). hIgE was desalted by gel filtration with PD-10 (Amersham Pharmacia Biotech AB) in 0.15 M KPO$_4$, 0.15 M NaCl, pH 7.8. To 0.95 mL (0.59 mg) hIgE were added 0.010 mL biotin-LC-Sulfo-NHS (3.59 mM, Pierce). Incubation then took place at room temperature for 1 hour, whereupon the coupling reaction was quenched by the addition of 40 µL of 2 M glycine. The mixture was then applied to a PD-10 gel filtration column equilibrated with 50 mM NaPO$_4$, 0.15 M NaCl, pH 7.4. Yields and final concentration were calculated from the radioactivity as I-125-labelled hIgE was included in the coupling. The concentration of hIgE was analyzed by immunochromatography and UniCAP tIgE (Pharmacia & Upjohn Diagnostics AB, Sweden).

Deposition of biotinylated IgE on application filter: To application filters 5×5 mm (Whatman F075-14) were dispensed 0.006 mL of biotinylated IgE (1.6 ng) diluted in 50 mM NaPO$_4$, 0.15 M NaCl, 6% BSA, 5% lactose, 5% dextran T5000, pH 7.4. The filters were dried at 30° C. for 1 hour.

Test procedure: Strips were mounted to a surface inclined about 16° from the bench plane. Sucking membranes (3.5 cm wide, Schleicher & Schuell, GB004) were placed 0.5 cm into the upper end of the membrane. To obtain constant pressure, metal weights were placed on the sucking membranes. Samples and reagents were then pipetted successively as described below. Each sample and reagent volume was sucked into the membrane before the following volume was pipetted.

1) 30 µL of 50 mM NaPO$_4$, 0.15 M NaCl, pH 7.4.
2) A filter with predeposited biotinylated IgE was placed at the bottom of the strip.
3) 30 µL of patient serum were pipetted to each filter.
4) 20 µL of test buffer (0.1 Na—PO$_4$, 0.15 M NaCl, 10% sucrose, 3% BSA, 0.05% bovine gammaglobulin, 0.05% NaN$_3$, pH 7.4) were added to the filter.
5) The application filter was removed.
6) 20 µL of detection conjugate (75 µg/ml) diluted in test buffer.
7) 2×30 µL of test buffer.
8) The fluorescence of the detection zone was measured as a response area (Vmm) with a scanning red laser fluorometer (635 nm).

Three positive t3-sera were selected and analysed in triplicate with three different conjugate batches. Signal areas obtained with nitrocellulose coated with different IgE particle concentrations (described in Example 1 above) run with conjugate 2 were used as a stored calibration curve.

PIC correction meant that the signal for the reaction zone for t3 was multiplied by PICexp/PICobs before reading against the stored calibration curve (master curve). PICexp was defined as the average of the PIC signals obtained in the run with conjugate 2.

| Serum | Conc (KU/L) Average of triplicate | | | Between CV (%) |
|---|---|---|---|---|
| | Conjugate 1 | Conjugate 2 | Conjugate 3 | |
| Reading against Master curve for uncorrected signal | | | | |
| 1 | 0.75 | 3.0 | 1.4 | 68 |
| 2 | 5.7 | 29.1 | 18.7 | 66 |
| 3 | 2.5 | 10.8 | 6.8 | 62 |
| Reading against master curve for PIC-corrected signal | | | | |
| 1 | 2.5 | 3.5 | 1.9 | 29 |
| 2 | 14.2 | 19.5 | 20.7 | 19 |
| 3 | 3.6 | 5.3 | 6.1 | 26 |

Between CV (%) is calculated as the variation of the three averages obtained for the different conjugates. The results show that the idea of a predeposited calibrator substance in the application zone is functional and that the use thereof as a PIC additionally gives a reduced between-assay-variation.

What is claimed is:

1. A lateral flow method for the determination of an analyte in a sample involving utilizing biospecific affinity reactions, and comprising the following steps:
   i. forming a complex in a lateral flow matrix, the complex comprising:
      Reactant I - - - Analyte' - - - Reactant*, where
      a. Reactant* and Reactant I exhibit biospecific affinity to the analyte,
      b. Reactant* is analytically detectable,
      c. Analyte' is the analyte or an analyte-related reactant, and subsequently
   ii. determining the detectable signal constituting a sample value from Reactant* in the complex, and
   iii. determining the amount of analyte in the sample by comparing the sample value with one or more calibrator values, each of which corresponds to a standard amount of analyte,
   wherein A) before determination of the calibrator value, either (i) calibrator, or (ii) a binder for the calibrator has been bound to a matrix, and when a binder for the calibrator has been bound to the matrix, calibrator is added or calibrator predeposited in the matrix is released for binding with the binder, and the matrix is insoluble in the liquid medium in which binding of Reactant* to the calibrator occurs, B) the calibrator and the analyte exhibit biospecific affinity to Reactant* by equivalent binding sites, C) two or more calibrator zones CZ comprising calibrator or binder for the calibrator are located in a single process flow stream with Reactant I in a detection zone (DZ), and D) all of the detection zones DZ are downstream of all of the calibrator zones CZ in the lateral flow matrix.

2. The method according to claim 1, wherein calibrator has been bound to the matrix before the determination of calibrator value.

3. The method according to claim 1, wherein a binder for the calibrator has been bound to the matrix before the determination of calibrator value.

4. The method according to claim 1, wherein the binder for the calibrator is one member of a specific binding pair, and the other member of the specific binding pair is coupled or conjugated to the calibrator.

5. The method according to claim 1, wherein
   a. (i) each calibrator zone comprises calibrator in an amount corresponding to a standard amount of analyte, or
   (ii) each calibrator zone contains calibrator binder, the amount of calibrator binder and the amount of calibrator corresponding to a standard amount of analyte, and
   b. Reactant* is bound to the calibrator by transporting Reactant* through the calibrator zones.

6. The method according to claim 1, wherein along a single matrix is the flow matrix, and wherein along a single process flow stream, there are
   a. two or more calibrator zones (CZ), each of which exhibits a matrix calibrator or a matrix calibrator binder,
   b. one or more detection zones (DZ), in which a Capturer is firmly anchored and is either Reactant I or a biospecific affinity reactant, which directly or indirectly binds Reactant I biospecifically,
   c. an application zone for Reactant*, $A_{R*}Z$, which is located upstream of said CZ and DZ and to which Reactant* is optionally predeposited, and
   d. an application zone for sample ($A_SZ$) which is located
      i. upstream of or coinciding with a detection zone,
      ii. downstream or upstream of or coinciding with $A_{R*}Z(A_SZ/A_{R*}Z)$, or
      iii. upstream of, downstream of or coinciding with a calibrator zone,
   wherein Reactant* is added to $A_{R*}Z$ if Reactant* is not predeposited, or buffer is added to $A_{R*}Z$ if Reactant* is predeposited, and sample is added to $A_SZ$, optionally premixed with Reactant* if $A_SZ$ and $A_{R*}Z$ coincide, such that analyte and Reactant* reach DZ at the same time, or such that analyte reaches DZ before Reactant*.

7. The method according to claim 6, wherein the calibrator zones CZ comprise a calibrator binder, and calibrator is predeposited upstream of the calibrator zones.

8. The method according to claim 6, wherein the process flow stream comprises two of said calibrator zones, and the level of analyte in the sample is obtained by:
   a. comparing a calibrator value from one of the calibrator zones located in the process flow stream including the detection zone, with one or more separately obtained calibrator values to determine a deviation between the measured calibrator value and the separately obtained calibrator values, and
   b. adjusting the sample value from the detection zone by the deviation, and subsequently obtaining the level of analyte in the sample by comparing the adjusted sample value with one or more of the separately obtained calibrator values.

9. The method according to claim 6, wherein
   a. $A_SZ$ is (i) common to $A_{R*}Z$, forming a common zone $A_SZ/A_{R*}Z$ or (ii) is located upstream of $A_{R*}Z$, and
   b. for alternative (i) sample is premixed with Reactant* before it is added to the common zone $A_SZ/A_{R*}Z$, or sample is added to the common zone $A_SZ/A_{R*}Z$ containing predeposited Reactant*, or for alternative (ii), sample is added to $A_SZ$, which is located upstream of $A_{R*}Z$ which in turn comprises predeposited Reactant*.

10. The method according to claim 5, wherein Reactant* has particles as an analytically detectable group, and/or calibrator or calibrator binder is/are anchored to the matrix by particles.

11. The method according to claim 1, wherein the analyte is an antibody directed to Reactant I or to Reactant*, and
    a. Reactant* is an antibody directed to the analyte and Reactant I is an antigen or hapten, when the analyte is an antibody directed to Reactant I, or
    b. Reactant* is an antigen or a hapten and Reactant I is an antibody directed to the analyte, when the analyte is an antibody directed to Reactant*.

12. The method according to claim 1, wherein the analyte is an antigen, and Reactant* and Reactant I are antibodies directed to the analyte.

13. The method according to claim 1, wherein the method is performed as a part of diagnosing allergy or autoimmune disease.

14. A device for transforming measured signal values of a complexed, analytically detectable reactant (Reactant*) to real amounts of analyte in a sample, in connection with performing an analysis method which utilizes biospecific affinity reactions for the determination of the amount of analyte in a sample, wherein the device comprises:
   a flow matrix in which there is an area of process flow for the transport of Reactant*, and wherein there are in said area
      i. two or more calibrator zones (CZ) comprising a calibrator, or binder for the calibrator, which is firmly anchored to the matrix, the amounts of calibrator or calibrator binder, respectively, being different for at least two calibrator zones and the calibrator exhibiting binding sites to which Reactant* binds, when Reactant* is transported through a calibrator zone,
      ii. an application zone for Reactant* ($A_{R*}Z$) upstream of said calibrator zones, and
      iii. one or more detection zones (DZ), all of the detection zones being downstream of all of the calibrator zones.

15. The device according to claim 14, wherein a calibrator binder is firmly anchored in the matrix and the device comprises calibrator predeposited upstream of the calibrator zones.

16. The device according to claim 14, wherein the device comprises Reactant* predeposited in $A_{R*}Z$.

17. The device according to claim 14, wherein the process flow comprises a detection zone (DZ) which is located downstream of $A_{R*}Z$ and comprises a firmly anchored Capturer to which Reactant* can bind in the DZ, and a zone of application of sample ($A_SZ$) which is located upstream of or coincides with said DZ.

18. The device according to claim 17, wherein $A_{R*}Z$ is located upstream of or downstream of or coincides with $A_SZ$.

19. The device according to claim 17, wherein the firmly anchored reactant (Capturer) has biospecific affinity to the analyte or to an analyte-related reactant.

20. The device according to claim 17, wherein the firmly anchored reactant (Capturer) has biospecific affinity to a second reactant which in turn has biospecific affinity to the analyte or to an analyte-related reactant.

21. The device according to claim 17, wherein $A_SZ$ is located upstream of all calibrator zones.

22. A test kit, comprising a device according to claim 14.

23. The kit according to claim 22, wherein the kit comprises Reactant*.

24. The kit according to claim 22, wherein the kit comprises calibrator when said device has the calibrator binder bound to the matrix.

25. The device according to claim 14, wherein Reactant* has biospecific affinity to analyte or an analyte-related reactant and to the calibrator.

26. The method according to claim 1, wherein Reactant* comprises a fluorophore group or a chromogenic group.

27. The method according to claim 1, wherein Reactant* comprises metal particles or nonmetal particles.

28. The method according to claim 1, wherein Reactant* comprises gold sol particles.

29. The device according to claim 14, wherein Reactant* comprises a fluorophore group or a chromogenic group.

30. The device according to claim 14, wherein Reactant* comprises metal particles or nonmetal particles.

31. The device according to claim 14, wherein Reactant* comprises gold sol particles.

* * * * *

UNITED STATES PATENT AND TRADEMARK OFFICE
CERTIFICATE OF CORRECTION

PATENT NO. : 6,916,666 B1
DATED : July 12, 2005
INVENTOR(S) : Ib Mendel-Hartvig

It is certified that error appears in the above-identified patent and that said Letters Patent is hereby corrected as shown below:

Column 18,
Line 33, change "sample, wherein" to -- sample, to form complexes comprising Reactant*in an amount which is related to the amount of analyte in the sample, wherein --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,916,666 B1 Page 1 of 1
DATED : July 12, 2005
INVENTOR(S) : Ib Mendel-Hartvig It is certified that error appears in the above-identified patent and that said Letters Patent is hereby corrected as shown below:

<u>Title page,</u>
Item [73], Assignee, should read -- Pharmacia Diagnostics AB --.

Signed and Sealed this

Eleventh Day of April, 2006

JON W. DUDAS
*Director of the United States Patent and Trademark Office*